(12) United States Patent
Hairabedian et al.

(10) Patent No.: US 11,065,165 B2
(45) Date of Patent: Jul. 20, 2021

(54) CHILD SANITARY NAPKIN METHOD AND APPARATUS

(71) Applicants: David Hairabedian, Irvine, CA (US); Patricia Ann Collins, Kansas City, MO (US); Joanna Hairabedian, Irvine, CA (US)

(72) Inventors: David Hairabedian, Irvine, CA (US); Patricia Ann Collins, Kansas City, MO (US); Joanna Hairabedian, Irvine, CA (US)

(*) Notice: Subject to any disclaimer, the term of this patent is extended or adjusted under 35 U.S.C. 154(b) by 73 days.

(21) Appl. No.: 16/550,200

(22) Filed: Aug. 24, 2019

(65) Prior Publication Data
US 2021/0052440 A1 Feb. 25, 2021

(51) Int. Cl.
| | |
|---|---|
| *A61F 13/84* | (2006.01) |
| *A61F 13/472* | (2006.01) |
| *A61F 13/539* | (2006.01) |
| *A61F 13/56* | (2006.01) |
| *A61F 13/475* | (2006.01) |

(Continued)

(52) U.S. Cl.
CPC ........ *A61F 13/8405* (2013.01); *A61F 13/475* (2013.01); *A61F 13/47245* (2013.01); *A61F 13/539* (2013.01); *A61F 13/5611* (2013.01); *A61F 2013/15715* (2013.01); *A61F 2013/4706* (2013.01); *A61F 2013/53035* (2013.01); *A61F 2013/530481* (2013.01); *A61F 2013/53908* (2013.01); *A61F 2013/842* (2013.01); *A61F 2013/8414* (2013.01); *A61F 2013/8479* (2013.01)

(58) Field of Classification Search
CPC .............. A61F 13/5605; A61F 13/5611; A61F 13/5616; A61F 13/47272; A61F 2013/5109; A61F 2013/8405; A61F 2013/8408; A61F 13/47245
See application file for complete search history.

(56) References Cited

U.S. PATENT DOCUMENTS

| | | | |
|---|---|---|---|
| 6,652,503 B1 * | 11/2003 | Bradley | A61F 13/47272 604/385.01 |
| 10,016,316 B2 * | 7/2018 | Sakaguchi | A61F 13/84 |

(Continued)

FOREIGN PATENT DOCUMENTS

| | | | | |
|---|---|---|---|---|
| WO | WO 9402099 A1 * | 2/1994 | ............ | A61F 13/74 |
| WO | WO 9925289 A1 * | 5/1999 | ............ | A61F 13/15 |

*Primary Examiner* — Susan S Su
(74) *Attorney, Agent, or Firm* — Edmond DeFrank (57) ABSTRACT

The embodiments disclose an apparatus including a child sanitary napkin including a disposable child sanitary napkin underwear, wherein the child sanitary napkin includes a waterproof non porous outer layer, an adhered superabsorbent polymer layer, an odor absorbing activated charcoal pad layer with a soft cotton covering layer, an imprinted product barcode and an embedded RFID chip for tracking the child via a digital device cellular connection, wherein the child sanitary napkin includes a shape contoured to a female anatomical groin area, wherein the child sanitary napkin includes flared front and rear terminus areas to increase an adhesive bonding area, wherein the child sanitary napkin includes sizes conforming to children's clothing and age sizes, and age appropriate decorative images including stickers to apply to the child sanitary napkin outer surface.

20 Claims, 11 Drawing Sheets

(51) Int. Cl.
    *A61F 13/53*         (2006.01)
    *A61F 13/15*         (2006.01)
    *A61F 13/47*         (2006.01)

(56) References Cited

U.S. PATENT DOCUMENTS

| | | | |
|---|---|---|---|
| 2002/0016579 A1* | 2/2002 | Stenberg | A61F 13/42 |
| | | | 604/361 |
| 2006/0293634 A1* | 12/2006 | Thomas | A61F 13/55145 |
| | | | 604/385.01 |
| 2008/0249494 A1* | 10/2008 | Digiacomantonio | |
| | | | A61F 13/53747 |
| | | | 604/378 |
| 2008/0294140 A1* | 11/2008 | Ecker | A61F 13/472 |
| | | | 604/385.23 |
| 2010/0160882 A1* | 6/2010 | Lowe | A61F 13/505 |
| | | | 604/361 |
| 2010/0256585 A1* | 10/2010 | Konawa | A61F 13/5611 |
| | | | 604/385.04 |
| 2011/0183712 A1* | 7/2011 | Eckstein | G06Q 30/016 |
| | | | 455/556.1 |
| 2012/0173249 A1* | 7/2012 | Popp | A61F 13/51496 |
| | | | 705/1.1 |
| 2012/0330261 A1* | 12/2012 | Reaume | A61F 13/476 |
| | | | 604/385.03 |
| 2015/0342795 A1* | 12/2015 | Alzate Machado | |
| | | | A61F 13/47245 |
| | | | 604/385.04 |
| 2016/0338881 A1* | 11/2016 | Hyppolite | A61F 13/15268 |
| 2017/0246045 A1* | 8/2017 | Schmoker | A61F 13/472 |
| 2018/0325750 A1* | 11/2018 | Vohwinkel | A61F 13/47245 |
| 2020/0188196 A1* | 6/2020 | Suh | A61F 13/5616 |

\* cited by examiner

CHILD SANITARY NAPKIN METHOD AND APPARATUS

BACKGROUND

The addition of more chemicals in our foods including preservatives and other carry-over chemicals including growth hormones used in raising meat animals and pesticides in plant cultivation has led to an increase in the premature onset of menstruation in young girls. This poses potential health and emotional risks to the young girls. Parenting then is faced with the stresses in combating the potential of robbing these young girls of their childhood in having to deal with the personal, social and normal childhood activities being interrupted by a more mature situation every month.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview

It should be noted that the descriptions that follow, for example, in terms of a child sanitary napkin method and apparatus is described for illustrative purposes and the underlying system can apply to any number and multiple types of child sanitary napkins. In one embodiment of the present invention, the child sanitary napkin method and apparatus can be configured using a standalone child sanitary napkin. The child sanitary napkin method and apparatus can be configured to include a child sanitary napkin and can be configured to include a disposable child's underwear with an integrated child sanitary napkin using the present invention.

The phrase "child maxi pad" used herein refers to a "child sanitary napkin" and the two phrases have the same meaning and are used interchangeably without any change in meaning.

The term "crotch" used herein refers to the part of the body where the legs join at the top, including the area around the genitals and has the same meaning as "groin" and are used interchangeably without any change in meaning.

General Overview

Figure 1:
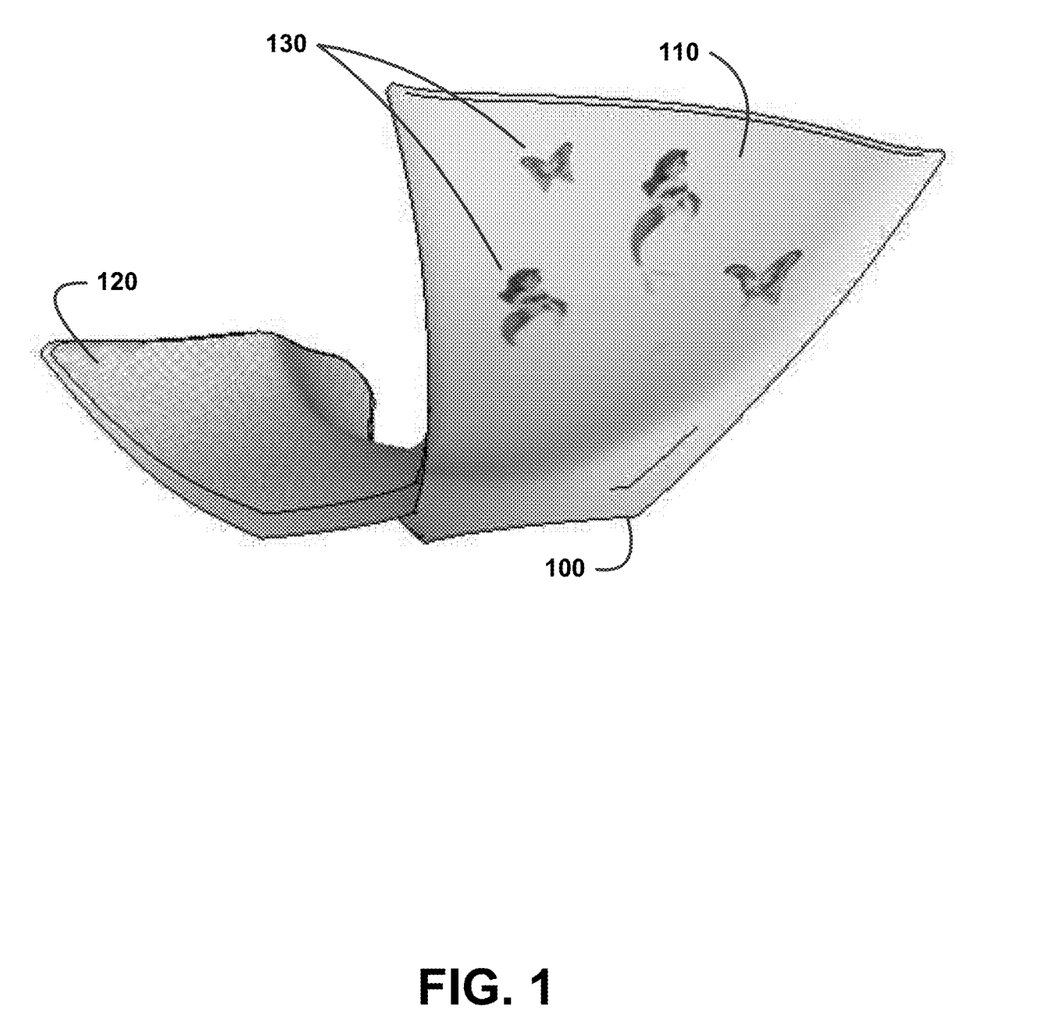
FIG. 1 shows for illustrative purposes only an example of a front prospective view of a child sanitary napkin apparatus of one embodiment.

FIG. 1 shows for illustrative purposes only an example of a front prospective view of a child sanitary napkin apparatus of one embodiment. FIG. 1 shows a front prospective view of a child sanitary napkin apparatus 100. The child sanitary napkin includes a waterproof non porous outer layer 110 with adhesive for attaching to inner underwear surface. The removable adhesive allows peeling the child sanitary napkin from the inner underwear surface for removal. An inner layer with a superabsorbent polymer layer is covered with a soft cotton covering 120. The soft cotton covering 120 is permanently adhered to the superabsorbent polymer layer on the surface of the superabsorbent polymer layer adjacent to the waterproof non porous outer layer 110. The soft cotton covering 120 loosely surrounds the balance of the superabsorbent polymer layer.

The soft cotton covering 120 adjacent to the waterproof non porous outer layer 110 is permanently adhered to the inner surface of the waterproof non porous outer layer 110. The adhesives used are non-toxic and non-allergenic and will not dissolve or denigrate their adhesive properties when they are in contact with liquids including human bodily fluids. The waterproof non porous outer layer 110 is a biodegradable plastic material. The waterproof non porous outer layer 110 with adhesive for attaching to inner underwear surface includes in one embodiment decorative age appropriate images 130 including stickers pre-adhered to the waterproof non porous outer layer 110. In another embodiment the child maxi pad 100 is packaged with decorative age appropriate image stickers with pre-applied adhesive covered with a cover sheet and the child or parent can utilize the stickers at their discretion. Decorative age appropriate images 130 and decorative age appropriate image stickers may include decals of various types, to include, but not limited to the following, flowers, animals, words of encouragement, images of inspiring characters, superheroes, etc.

Integrated into the child sanitary napkin apparatus 100 are sensors and communication devices. The sensors include but are not limited to sensors for monitoring a user's vital signs including pulse, respiratory rates, and blood pressure. The communication devices include but are not limited to devices for connection to Wi-Fi, Bluetooth, and the internet, a digital device including a smart phone, a cell phone, a digital tablet, and a computer. The communication devices also include a near-field communication device, a GPS locator, a transceiver and an automated 911 signal transmitter. The sensors and communication devices are coupled to at least one digital memory device, at least one digital processor, at least one artificial intelligence device, a printer, a digital image display device, and an audible alert device. Where applicable, sensors may include a glass breakage sensor, an accelerometer, a force detection device, a battery charge level detector, a light sensitive detector, and a temperature and humidity detector.

DETAILED DESCRIPTION

Figure 2:
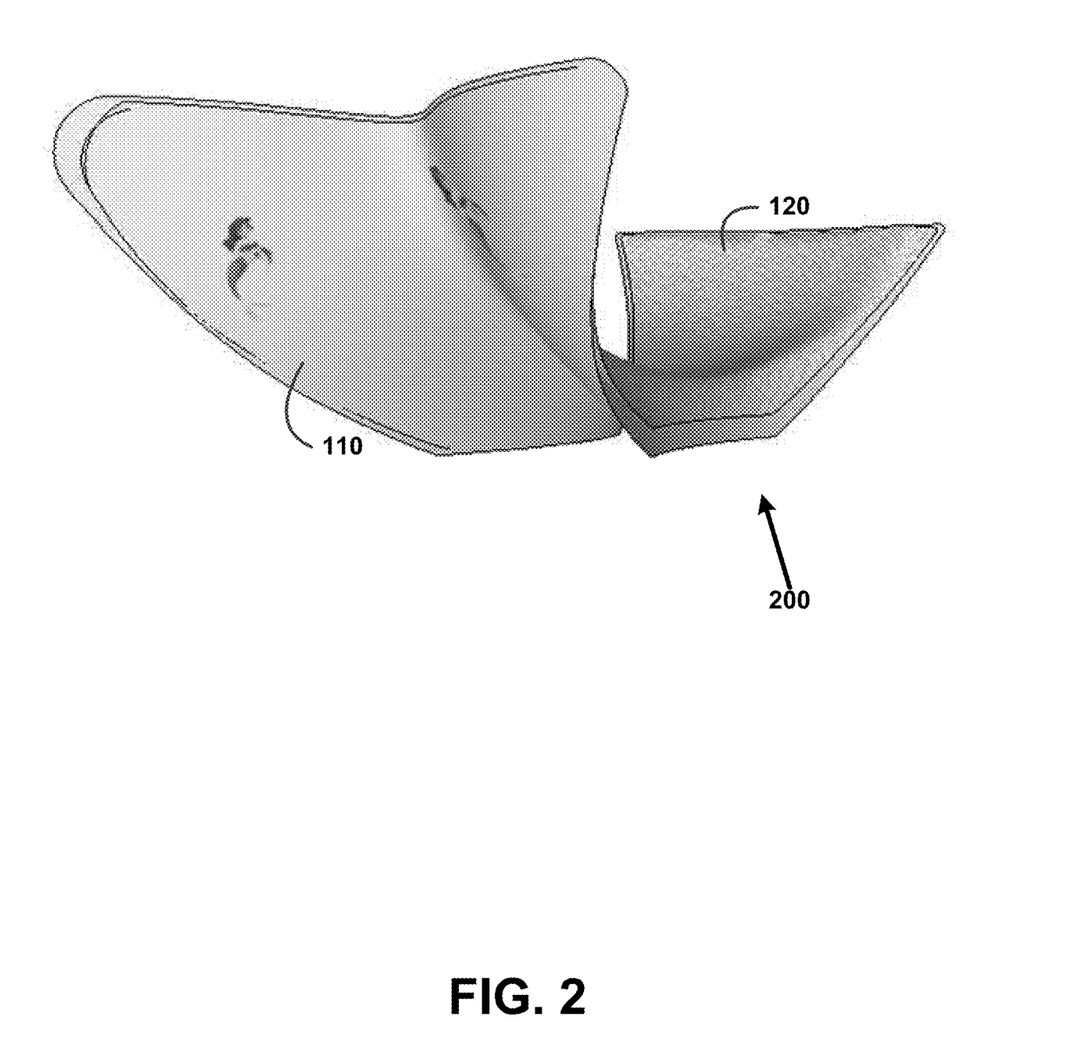
FIG. 2 shows for illustrative purposes only an example of a rear prospective view of child maxi pad of one embodiment.

FIG. 2 shows for illustrative purposes only an example of a rear perspective view of child maxi pad of one embodiment. FIG. 2 shows rear perspective view of child maxi pad 200. FIG. 2 also shows the waterproof non porous outer layer 110 with adhesive for attaching to inner underwear surface and superabsorbent polymer layer with a soft cotton covering 120. The waterproof non porous outer layer 110 with adhesive for attaching to inner underwear surface allows the user to secure the pad to a child's underwear. The superabsorbent polymer layer with a soft cotton covering 120 has a capacity to absorb even a heavy menstrual flow.

Figure 3:
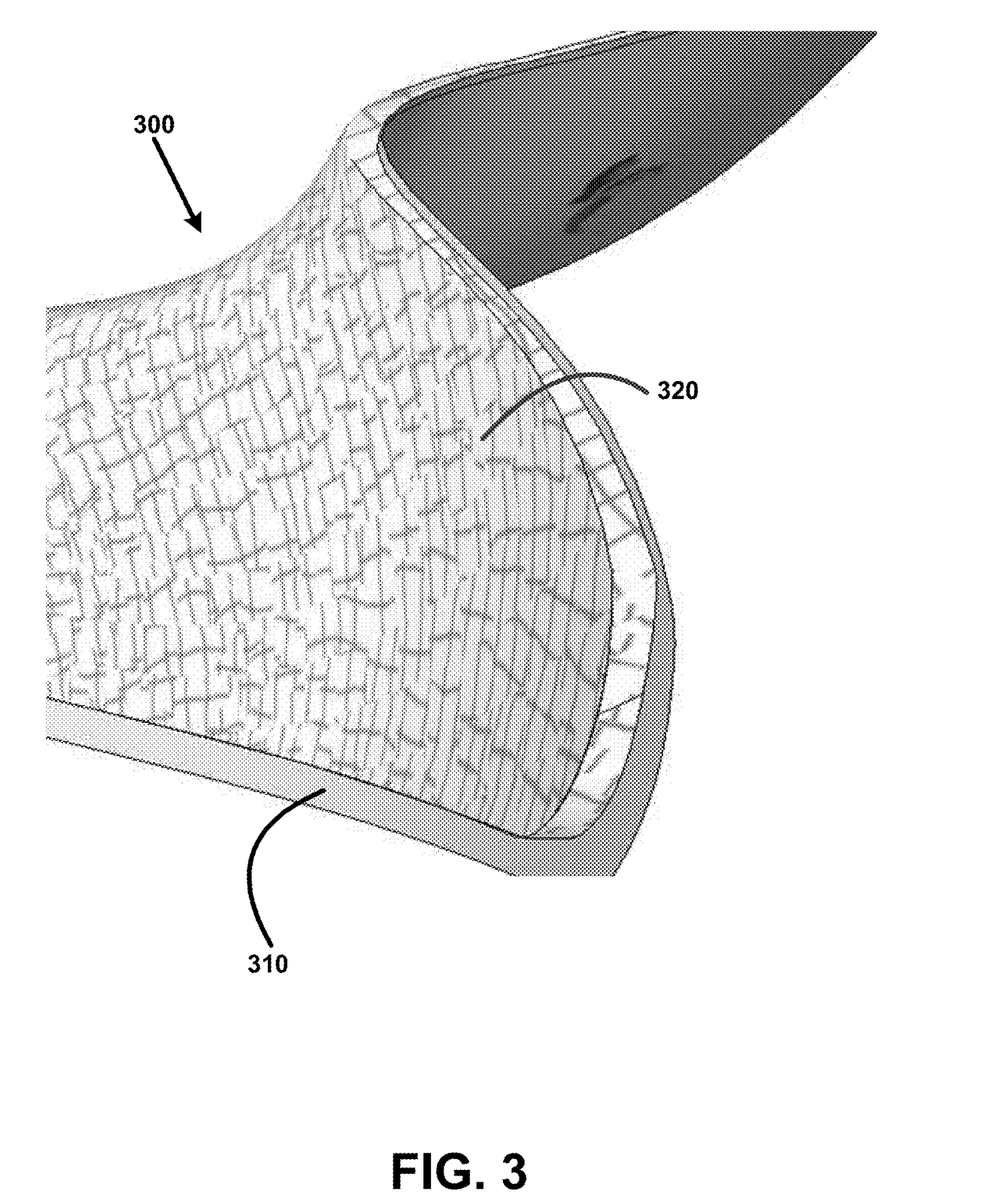
FIG. 3 shows for illustrative purposes only an example of a rear inner prospective view of child maxi pad of one embodiment.

Rear inner perspective view of child maxi pad:

FIG. 3 shows for illustrative purposes only an example of a rear inner perspective view of child maxi pad of one embodiment. FIG. 3 shows a rear inner perspective view of child maxi pad 300 with a waterproof non porous outer layer 310 and a thin superabsorbent polymer layer with an odor absorbing activated charcoal pad and a soft cotton covering 320. Showing is an example of the waterproof non porous outer layer 310 and thin superabsorbent polymer layer with an odor absorbing activated charcoal pad and a soft cotton covering 320 in a close up view. The rear inner perspective view illustrates in one embodiment a contour to closely fit the rear buttock crease to prevent leakage.

Figures 4A, 4B, 4C:
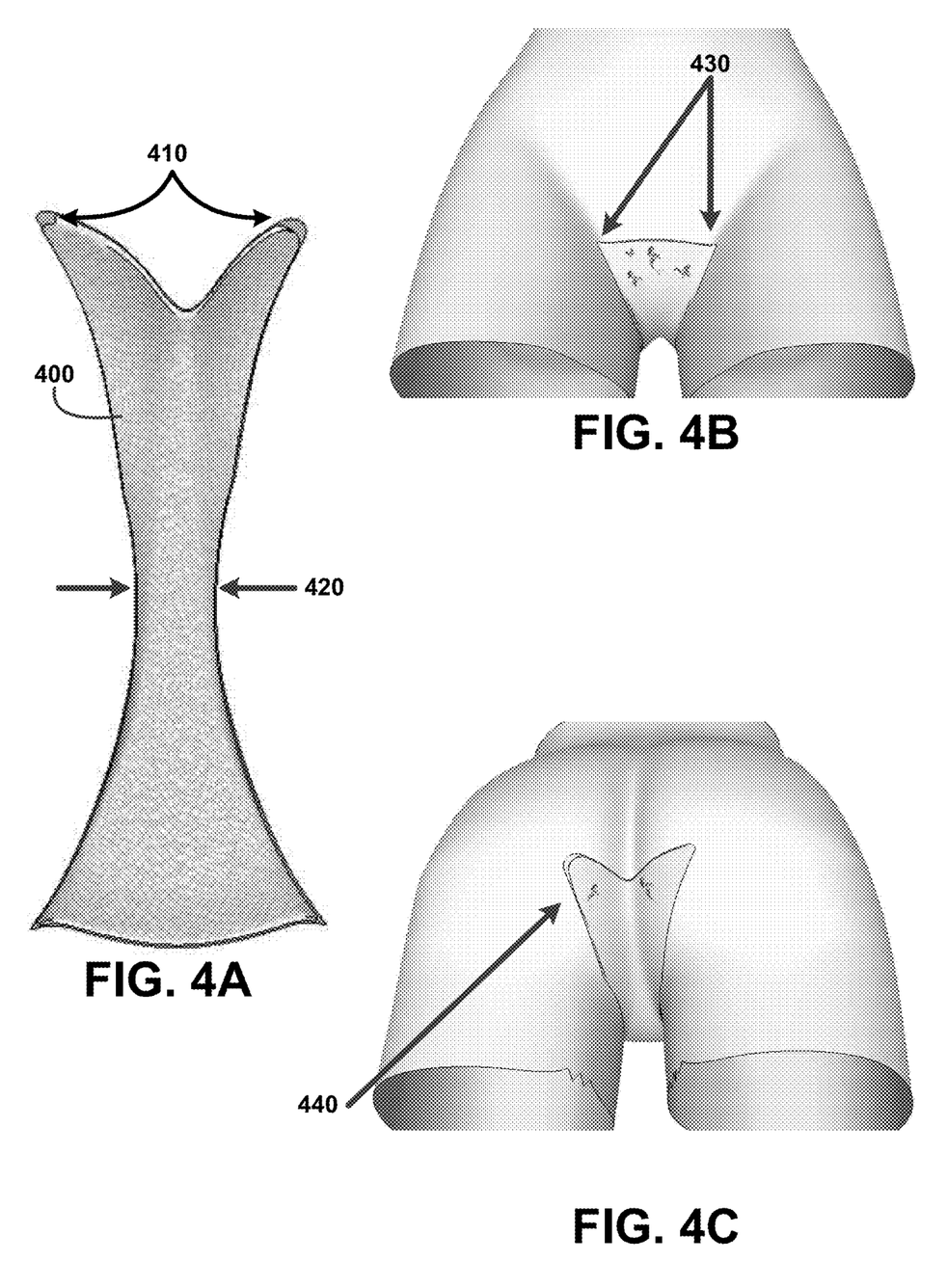
FIG. 4A shows for illustrative purposes only an example of top inner view of child maxi pad of one embodiment.
FIG. 4B shows for illustrative purposes only an example of a front flared end of one embodiment.
FIG. 4C shows for illustrative purposes only an example of a rear flared end of one embodiment.

Top Inner View of Child Maxi Pad:

FIG. 4A shows for illustrative purposes only an example of a top inner view of child maxi pad of one embodiment. FIG. 4A shows a top inner view of child maxi pad 400 showing flared ends 410 to increase adhesive bonding area to prevent slippage during physical activities. The child maxi pad shape includes a narrowing contour 420 in the crotch area for comfort and physical fit and superabsorbent polymer with a slight increase in thickness to increase localized absorption capacity to prevent leakage.

Front Flared End:

FIG. 4B shows for illustrative purposes only an example of a front flared end of one embodiment. FIG. 4B shows a front flared end sized to approximate a leg creases fit 430. A leg crease fit will create a snug fit to prevent leakage wherein the natural pressure of the tissue on both sides of the leg crease will snug the edge of the child sanitary napkin in each leg crease to create a tighter seal to prevent leakage.

Rear Flared End:

FIG. 4C shows for illustrative purposes only an example of a rear flared end of one embodiment. FIG. 4C shows the child maxi pad rear flared end 440 with slightly excess center material to accommodate butt hugging fit jeans and shorts to fit into the crease between the buttocks.

Figure 5:
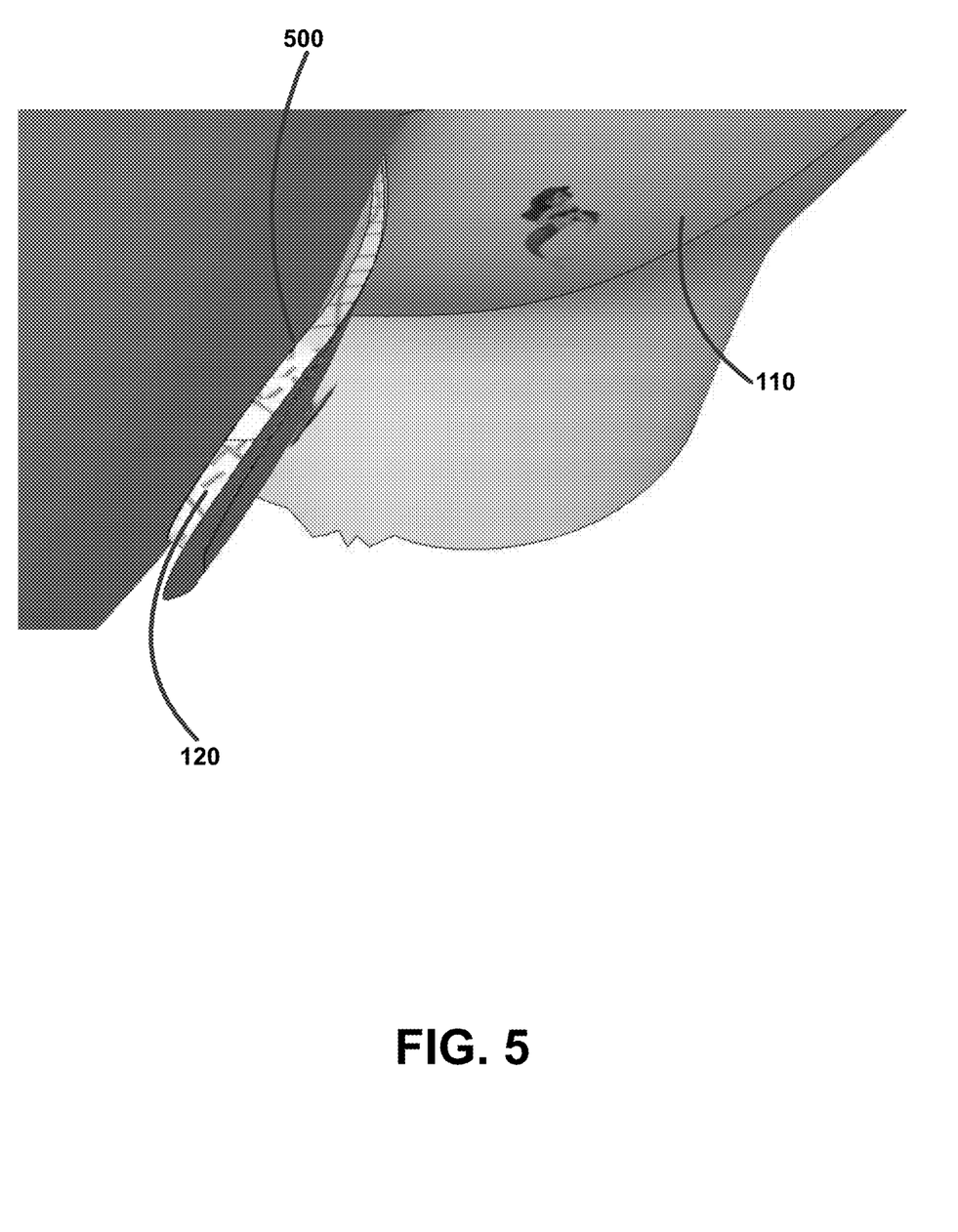
FIG. 5 shows for illustrative purposes only an example of a snug fit to prevent leakage of one embodiment.

Snug Fit to Prevent Leakage:

FIG. 5 shows for illustrative purposes only an example of a snug fit to prevent leakage of one embodiment. FIG. 5 shows the child maxi pad 500 snug fit to prevent leakage. Also shown are the waterproof non porous outer layer 110 with adhesive for attaching to inner underwear surface and superabsorbent polymer layer with a soft cotton covering 120. The child maxi pad is sized according to children's clothing and age sizes to provide a snug fit to prevent leakage. All age 7 girls are not the same size. Manufacturing a full range of sizes provides the parents the opportunity to fit the pad to the child and not endure the one size fits all frustrations.

Figure 6A:
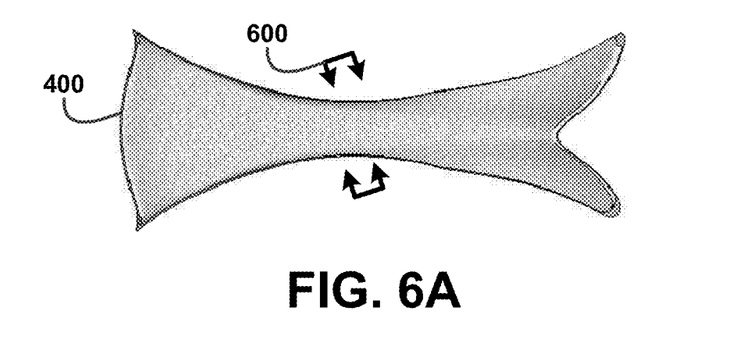
FIG. 6A shows for illustrative purposes only an example of a top inner view of child maxi pad cross section of one embodiment.

Top Inner View of Child Maxi Pad Cross Section:

FIG. 6A shows for illustrative purposes only an example of a top inner view of child maxi pad cross section of one embodiment. FIG. 6A shows a top inner view of child maxi pad cross section 600 of the top inner view of child maxi pad 400 that is referenced in FIG. 6B and FIG. 6C.

Figure 6B:
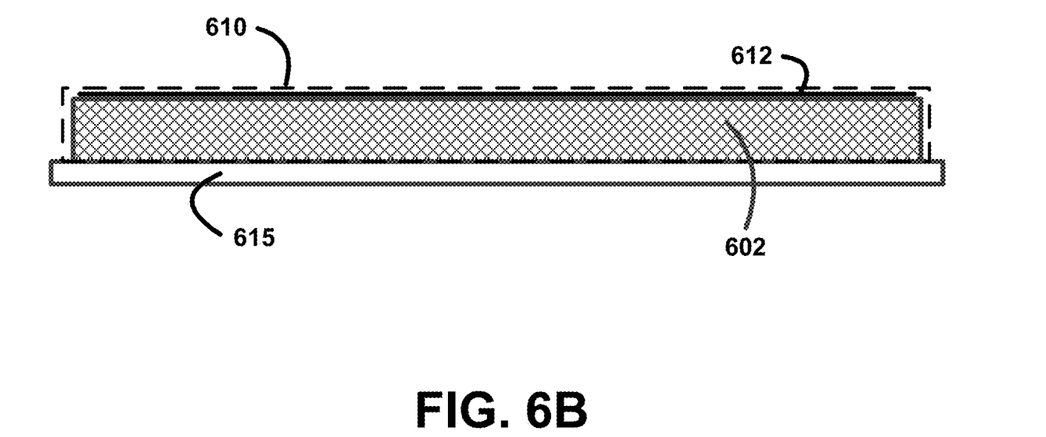
FIG. 6B shows for illustrative purposes only an example of a loose fit soft cotton cover of one embodiment.

Loose fit soft cotton cover:

FIG. 6B shows for illustrative purposes only an example of loose fit soft cotton cover of one embodiment. FIG. 6B shows a cross section 615 of the waterproof non porous outer layer, dry thin superabsorbent polymer layer cross section 602, an odor absorbing activated charcoal pad 612 with an antimicrobial-antibacterial treatment approximately 1/32" thick and loose fit soft cotton cover cross section 610. The waterproof non porous outer layer prevents leakage to the underwear. The dry thin superabsorbent polymer layer is less bulky than a typical women's pad. The loose fit soft cotton cover serves to provide a comfortable surface to the vaginal skin and barrier between the superabsorbent polymer and vaginal skin.

Figure 6C:
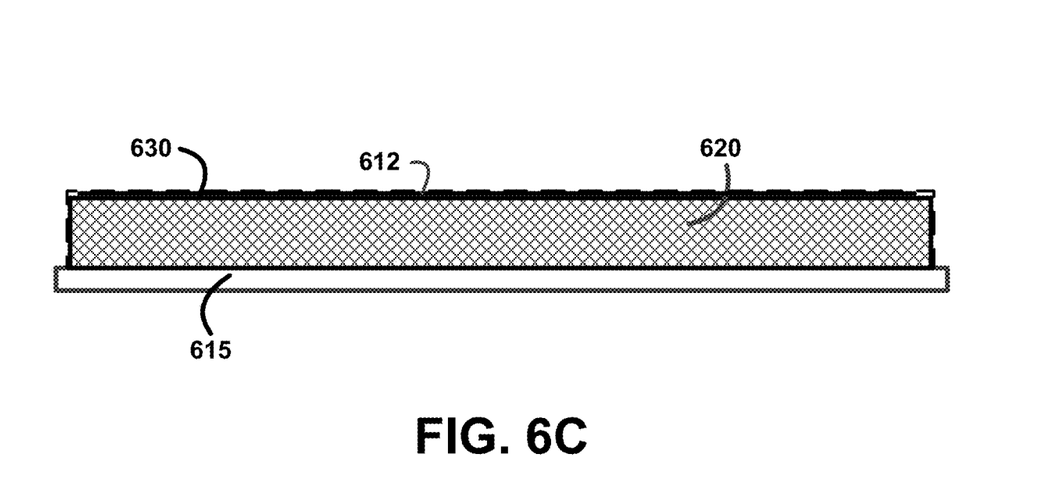
FIG. 6C shows for illustrative purposes only an example of a loose fitting cotton cover restraint against swelling of one embodiment.

Soft Cotton Cover Restrains Swelling:

FIG. 6C shows for illustrative purposes only an example of a soft cotton cover restraint against swelling of one embodiment. FIG. 6C shows the waterproof non porous outer layer cross section 615. A thin superabsorbent polymer layer swells as it retains menstrual flow, shown as swollen cross section 620. The odor absorbing activated charcoal pad 612 remains in place between the thin superabsorbent polymer layer and loose fitting soft cotton cover and does not interfere with the passage of menstrual fluids to the thin superabsorbent polymer layer. The loose fitting soft cotton cover 630 restrains swelling of superabsorbent polymer layer cross section. The waterproof non porous outer layer prevents any fluid from passing through the pad. The superabsorbent polymer expands in size as it retains more and more of the menstrual flow. Unchecked it can increase in thickness. This expansion in thickness can become uncomfortable and disconcerting to a young girl. The soft cotton cover 630 restrains swelling of superabsorbent polymer layer with the initial loose fit. As the superabsorbent polymer is constrained in its expansion it does not release the retained fluid.

Figure 7A:
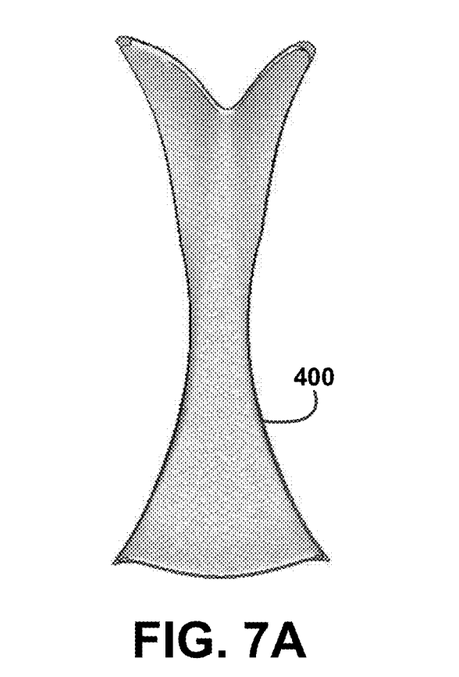
FIG. 7A shows for illustrative purposes only an example of a child maxi pad contoured shape of one embodiment.

Child Maxi Pad Contoured Shape:

FIG. 7A shows for illustrative purposes only an example of a child maxi pad contoured shape of one embodiment. FIG. 7A shows a top inner view of child maxi pad 400. A typical women's sanitary napkin is rectangular. A female crotch region is not rectangular so the typical women's sanitary napkin pad includes excess materials that can extend beyond the underwear and show as a bulge in the pants being worn or extend outside of some shorts styles. The child maxi pad contoured design fits the physiology of a female and prevents bulges or exposure of the pad outside the clothing. It further is a more comfortable fit.

Figure 7B:
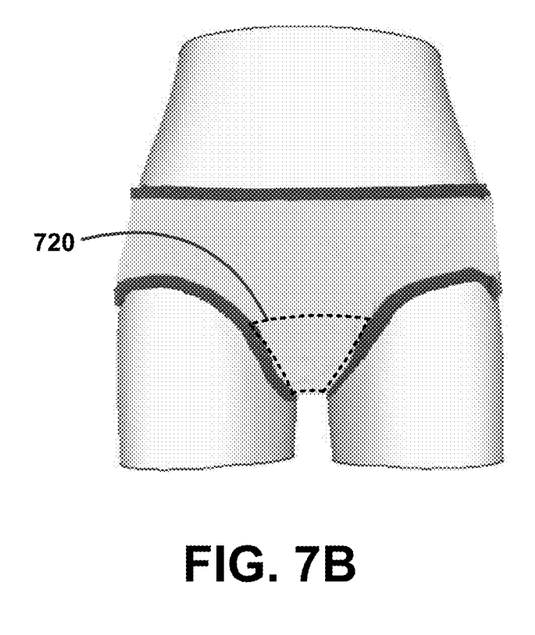
FIG. 7B shows for illustrative purposes only an example of a pad hidden beneath child's underwear of one embodiment.

Pad Hidden Beneath Child's Underwear:

FIG. 7B shows for illustrative purposes only an example of a pad hidden beneath child's underwear. FIG. 7B shows the reduced size and contoured shape of the child maxi pad 720 allow a child's underwear to hide the pad beneath. This prevents the child from enduring peer finger pointing and verbal abuse.

Figure 8A:
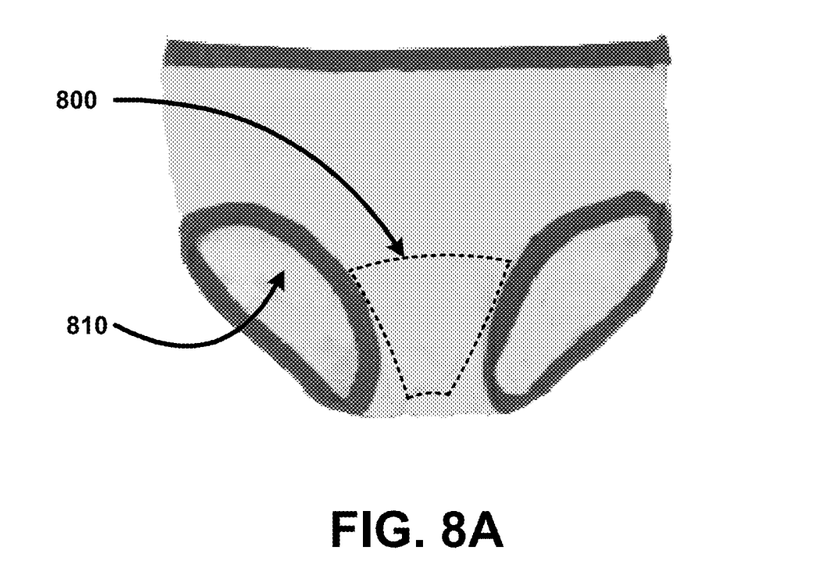
FIG. 8A shows for illustrative purposes only an example of an incorporated child maxi pad of one embodiment.

An Incorporated Child Maxi Pad:

FIG. 8A shows for illustrative purposes only an example of an incorporated child maxi pad of one embodiment. FIG. 8A shows a system including a disposable child sanitary napkin underwear 810 and a child maxi pad 800. The disposable child underwear 810 is made using a waterproof reinforced paper based fabric. During time outside the home, including school, the child can carry spare disposable child sanitary napkin underwear in her backpack. Particularly very young girls would not have to deal with the handling of a soiled pad. The very young girls would have already gone through the transition of diapers to toddler panties. This can make this transition "old school" for the parents to explain and ease any stress that could be experienced by the very young girl.

Figure 8B:
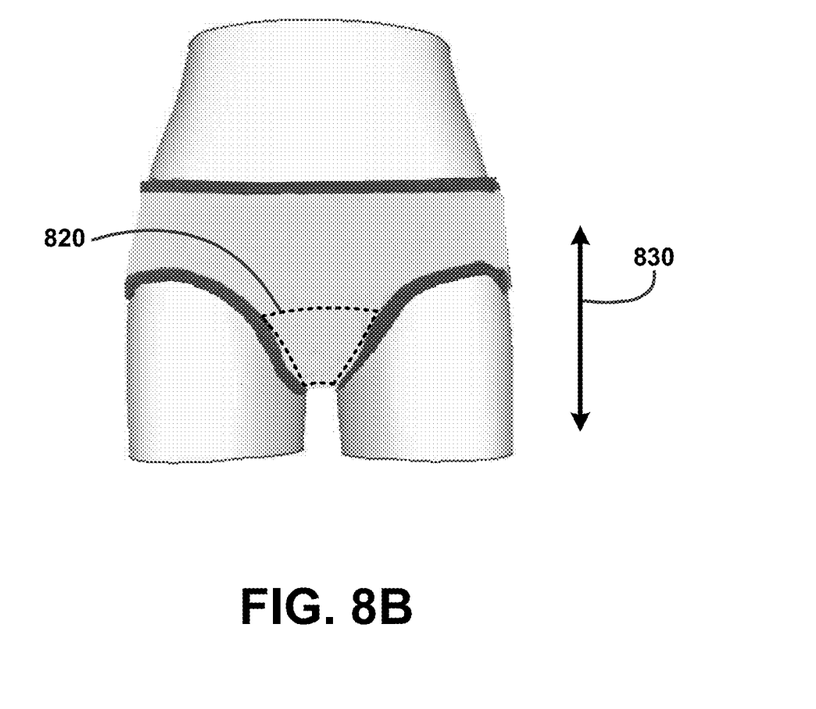
FIG. 8B shows for illustrative purposes only an example of a disposable child sanitary napkin underwear of one embodiment.

Disposable Child Sanitary Napkin Underwear:

FIG. 8B shows for illustrative purposes only an example of a disposable child sanitary napkin underwear of one embodiment. FIG. 8B shows where a disposable child sanitary napkin underwear enables a young child aged 5-9 to easily pull-down and pull-up the underwear and pad when going to the bathroom eliminating the stress of dealing with a separate pad 820. A child pulling down and up (denoted by arrow 830) the disposable child sanitary napkin underwear is essentially the same as the child would be doing with a regular pair of child underwear.

Figure 9:
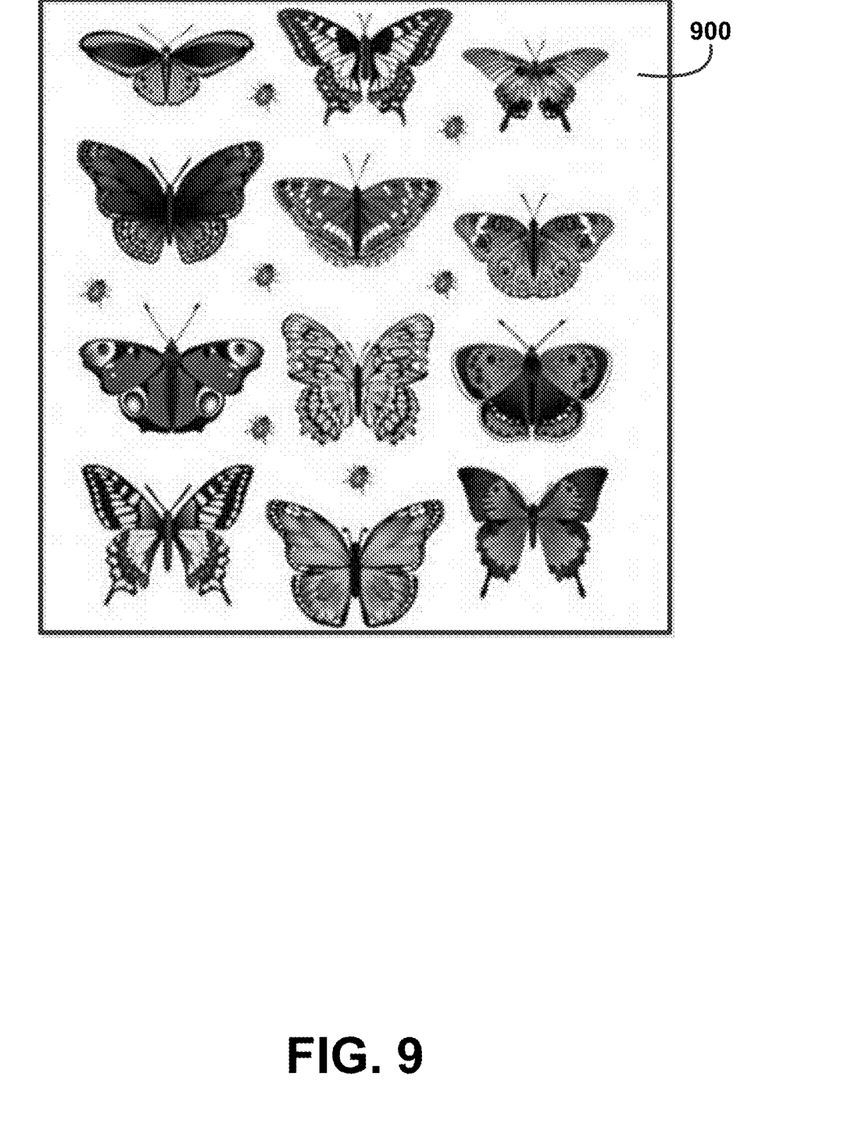
FIG. 9 shows for illustrative purposes only an example of child sanitary napkin stickers of one embodiment.

Child Sanitary Napkin Stickers:

FIG. 9 shows for illustrative purposes only an example of child sanitary napkin stickers. FIG. 9 shows age appropriate decorative images 900 including stickers for example a sheet of butterfly stickers. The mother can assist the child in peeling and applying the stickers to the child sanitary napkin outer surface. This will add fun to the process of adapting the child to the use of the child sanitary napkin and relieve some of the fear and anxiety that otherwise may develop.

Figure 10A:
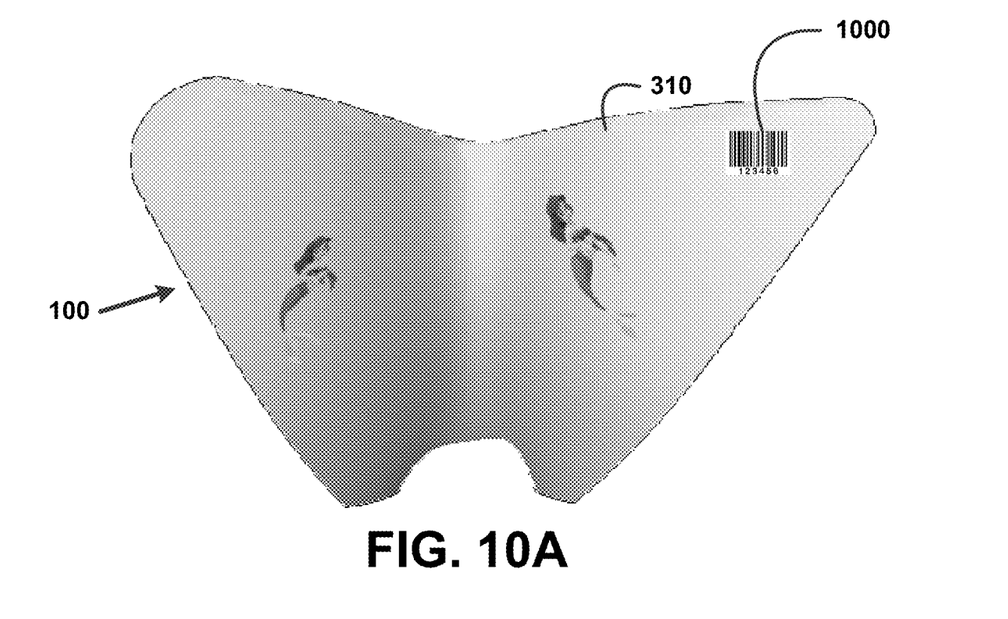
FIG. 10A shows for illustrative purposes only an example of a child maxi pad bar code of one embodiment.

Child maxi pad bar code:

FIG. 10A shows for illustrative purposes only an example of a child maxi pad bar code. FIG. 10A shows the child maxi pad 100 with a product bar code 1000 printed on the outer surface of the waterproof non porous outer layer 310. A parent can scan the barcode with a smart phone camera to facilitate reordering the child maxi pad 100 for their daughter.

Figure 10B:
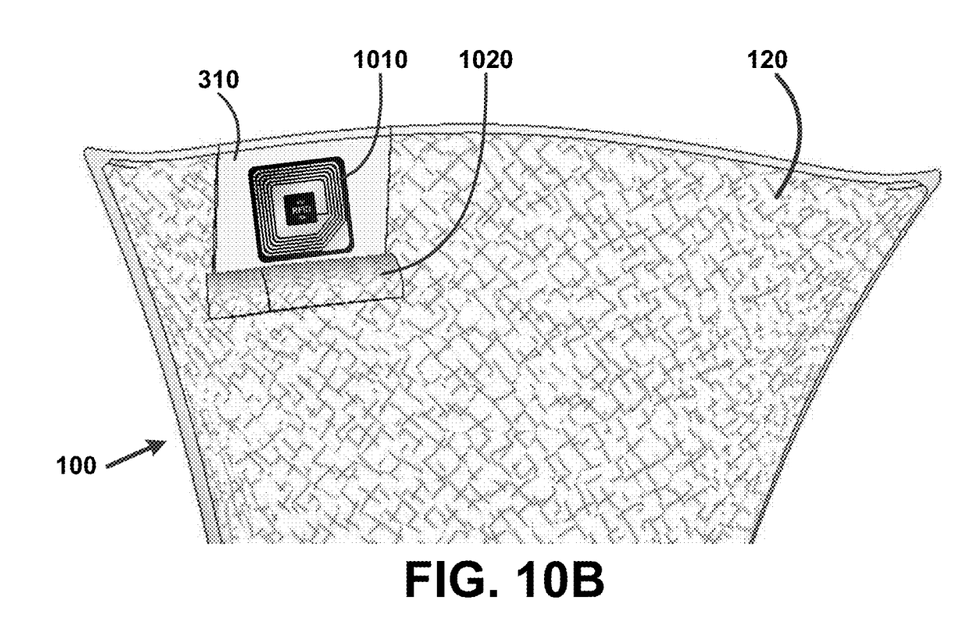
FIG. 10B shows for illustrative purposes only an example of a child maxi pad RFID of one embodiment.

Child Maxi Pad RFID Chip:

FIG. 10B shows for illustrative purposes only an example of a child maxi pad RFID. FIG. 10B shows a section of the interior surface of the waterproof non porous outer layer 310 of the child maxi pad 100 with the thin superabsorbent polymer layer with an odor absorbing activated charcoal pad and a soft cotton covering peeled back flap 1020 to expose an embedded RFID chip 1010. In this embodiment the RFID chip 1010 is a radio-frequency identification chip configured to transmit a signal to a digital device carried or worn by the child. The digital device may include a smart phone, a smart watch device, a digital tablet or other device with cellular connectivity. A parent can track the location of the child through the child's digital device using a parent's digital device including for example a smart phone. Should the child wearing the child maxi pad 100 with the embedded RFID chip 1010 be separated from their digital device the reception of the RFID chip 1010 signal will be cut-off. The parent will know something has happened that should not have happened and can investigate immediately.

Figure 11:
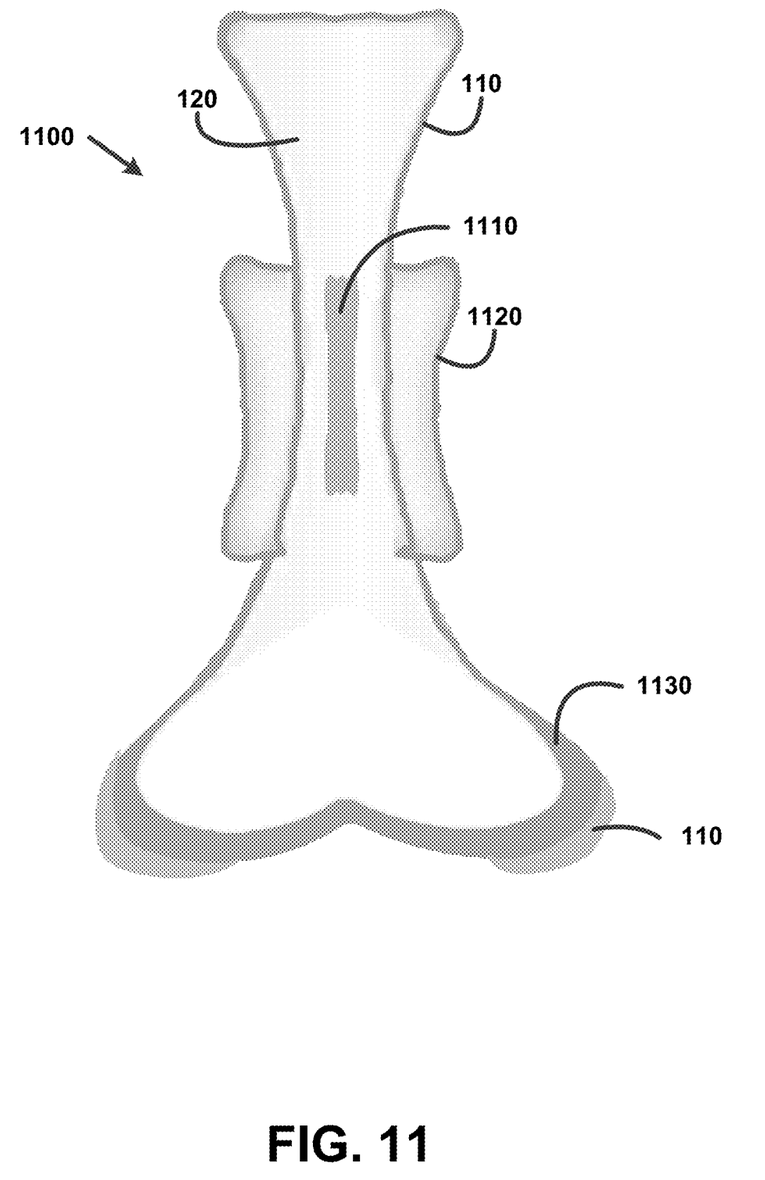
FIG. 11 shows for illustrative purposes only an example of a child maxi pad with side panels of one embodiment.

Child Maxi Pad with Side Panels:

FIG. 11 shows for illustrative purposes only an example of a child maxi pad with side panels. FIG. 11 shows in another embodiment a child maxi pad 1100 with side panels. The side panel 1120 is an extension of the pad narrowing portion. The side panel 1120 is narrow for fitting into the leg-groin crease to prevent overflow in that region of menstrual discharge. Also showing is the waterproof non porous outer layer 110 with adhesive for attaching to inner underwear surface and superabsorbent polymer layer with a soft cotton covering 120. A vaginally positioned double layer 1110 of superabsorbent polymer layer with an odor absorbing activated charcoal pad and a soft cotton covering provides added volume capacity to absorb vaginal discharge. A raised pad perimeter ridge 1130 of superabsorbent polymer layer with an odor absorbing activated charcoal pad adds additional leakage and odor protection.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
fabricating a system including a child sanitary napkin including disposable child sanitary napkin underwear;
wherein fabricating the child sanitary napkin includes a plurality of layers including an exterior waterproof non porous outer layer, a thin superabsorbent polymer layer, an odor absorbing activated charcoal pad layer and an interior soft cotton covering layer;
wherein fabricating the child sanitary napkin includes imprinting a product barcode on an outer surface of the waterproof non porous outer layer and embedding an RFID chip into the plurality of layers for tracking a wearer's location via a digital device cellular connection;
contouring a shape of the child sanitary napkin to conform to a female anatomical groin area;
flaring front and rear terminus areas of the child sanitary napkin to increase an adhesive bonding area;
fabricating the child sanitary napkin according to children's clothing and age sizes for providing a snug fit to prevent leakage; and
applying to the outer surface at least one decorative image.

2. The method of claim 1, further comprising flaring a front end for conforming to groin leg creases for creating a snug fit to prevent leakage.

3. The method of claim 1, wherein fabricating the waterproof non porous outer layer includes using a biodegradable plastic material.

4. The method of claim 1, further comprising adding excess material to the rear terminus area to fit into an intergluteal cleft of the wearer.

5. The method of claim 1, further comprising surrounding the superabsorbent polymer layer with non-adhered sections of the soft cotton covering configured to loosely surround the balance of the superabsorbent polymer layer and odor absorbing activated charcoal pad layer for restraining swelling of the superabsorbent polymer layer.

6. The method of claim 1, further comprising adhering each of the superabsorbent polymer layer and the soft cotton covering layer permanently to an inner surface of the waterproof non porous outer layer.

7. The method of claim 1, wherein the child sanitary napkin includes non-toxic and non-allergenic adhesives.

8. The method of claim 1, further comprising using adhesives that will not dissolve or denigrate when in contact with human bodily fluids.

9. The method of claim 1, wherein the disposable child sanitary napkin underwear is made of a waterproof reinforced paper based fabric, and wherein the disposable child sanitary napkin underwear is an additional layer adhered to the outer surface of the waterproof non porous outer layer.

10. The method of claim 1, wherein the disposable child sanitary napkin underwear is configured to allow a young female child to easily pull-down and pull-up the disposable child sanitary napkin underwear when going to the bathroom.

11. An apparatus, comprising:
a child sanitary napkin and a disposable underwear forming a disposable child sanitary napkin underwear;
wherein the child sanitary napkin includes a waterproof non porous outer layer, a superabsorbent polymer layer, an odor absorbing activated charcoal pad layer, a soft cotton covering layer, an imprinted product barcode and an embedded RFID chip for tracking a wearer via a digital device cellular connection, wherein the superabsorbent polymer layer is adhered to at least one of the waterproof non porous outer layer, the odor absorbing activated charcoal pad layer, and the soft cotton covering layer;
wherein the child sanitary napkin includes a shape contoured to a female anatomical groin area;
wherein the child sanitary napkin includes flared front and rear terminus areas to increase an adhesive bonding area;
wherein the child sanitary napkin is made in sizes conforming to children's clothing and age sizes; and
wherein the child sanitary napkin includes decorative images including stickers applied to the child sanitary napkin outer surface.

12. The apparatus of claim 11, further comprising non-toxic and non-allergenic adhesives to adhere an outer surface of the waterproof non porous outer layer non permanently to a child's underwear and permanently adhere the superabsorbent polymer layer with a soft cotton covering to an inner surface of the waterproof non porous outer layer.

13. The apparatus of claim 11, wherein the child sanitary napkin includes narrow side panel extensions, the flared front terminus area conforms to groin leg creases of the wearer for creating a snug fit to prevent leakage and the rear flared terminus area comprises excess material to fit into an intergluteal cleft of the wearer.

14. The apparatus of claim 11, wherein the waterproof non porous outer layer is made of a biodegradable plastic material.

15. The apparatus of claim 11, wherein the soft cotton covering layer is configured to be loose fitting over the superabsorbent polymer layer and the odor absorbing activated charcoal pad layer to restrain swelling of the superabsorbent polymer layer when absorbing a menstrual flow.

16. An apparatus, comprising:
a child sanitary napkin configured to conform to a female anatomical groin area, the child sanitary napkin including flared ends and a crotch portion with narrow side panels;
wherein the child sanitary napkin includes a biodegradable plastic material forming a waterproof non porous outer layer, an absorbent pad made of a superabsorbent polymer layer, an odor absorbing pad layer made of an activated charcoal with an antimicrobial-antibacterial treatment, and a soft cotton covering surrounding the superabsorbent polymer layer and the odor absorbing pad layer, at least one non-toxic and non-allergenic adhesive, an imprinted product barcode, and an embedded RFID chip for tracking a wearer via a digital device cellular connection;
a waterproof reinforced paper based fabric forming a disposable child underwear for attaching the child sanitary napkin to the disposable child underwear and forming a disposable child sanitary napkin underwear; and
a plurality of decorative images including stickers applied to an outer surface of the waterproof non porous outer layer outer surface.

17. The apparatus of claim 16, wherein the at least one non-toxic and non-allergenic adhesive is used to adhere the waterproof non porous outer layer outer surface non-permanently to a child's underwear and permanently adhere the superabsorbent polymer layer to the soft cotton covering and to an inner surface of the waterproof non porous outer layer.

18. The apparatus of claim 16, wherein the flared ends include a front flared end contoured to conform to groin leg creases to create a snug fit to prevent leakage.

19. The apparatus of claim 16, wherein the flared ends include a rear flared end with added material to fit into an intergluteal cleft of the wearer to accommodate butt hugging fit jeans and shorts.

20. The apparatus of claim 16, wherein the superabsorbent polymer layer is thicker in the crotch portion than in the flared ends of the absorbent pad to increase localized absorption capacity to prevent leakage.

* * * * *